(12) United States Patent
Kajitani

(10) Patent No.: US 8,806,947 B2
(45) Date of Patent: Aug. 19, 2014

(54) ULTRASONIC WAVE PROPAGATION TIME MEASUREMENT SYSTEM

(75) Inventor: Hiroshi Kajitani, Tokyo (JP)

(73) Assignee: NEC Corporation, Tokyo (JP)

( * ) Notice: Subject to any disclaimer, the term of this patent is extended or adjusted under 35 U.S.C. 154(b) by 420 days.

(21) Appl. No.: 13/203,196

(22) PCT Filed: Feb. 24, 2010

(86) PCT No.: PCT/JP2010/052863
§ 371 (c)(1),
(2), (4) Date: Aug. 24, 2011

(87) PCT Pub. No.: WO2010/098346
PCT Pub. Date: Sep. 2, 2010

(65) Prior Publication Data
US 2011/0303014 A1    Dec. 15, 2011

(30) Foreign Application Priority Data

Feb. 25, 2009   (JP) ................................. 2009-042127

(51) Int. Cl.
*G01N 29/00*   (2006.01)
(52) U.S. Cl.
USPC ............................................. 73/632; 73/597
(58) Field of Classification Search
CPC ... G01N 29/00; G01N 29/22; G01N 29/2412; G01N 29/4436; B06B 1/08
USPC ........ 73/584, 597, 632, 643; 702/39; 367/128
See application file for complete search history.

(56) References Cited

U.S. PATENT DOCUMENTS

| 4,297,607 A | * | 10/1981 | Lynnworth et al. | ........... 310/334 |
| 4,814,552 A | * | 3/1989 | Stefik et al. | ................ 178/19.02 |
| 4,991,148 A | * | 2/1991 | Gilchrist | ........................ 367/124 |
| 5,339,259 A | * | 8/1994 | Puma et al. | .................... 702/153 |
| 5,372,138 A | * | 12/1994 | Crowley et al. | ................ 600/463 |
| 5,421,338 A | * | 6/1995 | Crowley et al. | ................ 600/463 |
| 5,515,853 A | * | 5/1996 | Smith et al. | ................... 600/437 |

(Continued)

FOREIGN PATENT DOCUMENTS

| JP | 58-69536 A | 4/1983 |
| JP | 8-256396 A | 10/1996 |

(Continued)

OTHER PUBLICATIONS

Tetsuji et al. (English Translation of Japanese Patent Application Publication JP 2004-108826).*

(Continued)

*Primary Examiner* — Peter Macchiarolo
*Assistant Examiner* — Samir M Shah
(74) *Attorney, Agent, or Firm* — Sughrue Mion, PLLC

(57) ABSTRACT

An ultrasonic wave propagation time measurement system comprises: a transmitting section that transmits an electromagnetic wave signal indicating transmission timing and an ultrasonic wave signal, and a receiving section that detects the transmitted electromagnetic wave signal and the ultrasonic wave signal and calculates an ultrasonic wave propagation time based on reception times of the electromagnetic wave signal and the ultrasonic wave signal; and an initial mode setting mechanism that constitutes an optimum ultrasonic wave transmission/reception system by selecting the set values of one or more setting parameters is provided in a controlling unit that controls the transmission of the signals in the transmitting section and in a data processing unit that controls the detection and calculation in receiving section.

20 Claims, 10 Drawing Sheets

(56) References Cited

U.S. PATENT DOCUMENTS

| | | | |
|---|---|---|---|
| 5,517,579 A * | 5/1996 | Baron et al. | 382/187 |
| 5,524,630 A * | 6/1996 | Crowley | 600/466 |
| 5,588,432 A * | 12/1996 | Crowley | 600/439 |
| 5,715,825 A * | 2/1998 | Crowley | 600/462 |
| 5,750,941 A * | 5/1998 | Ishikawa et al. | 178/19.02 |
| 5,840,031 A * | 11/1998 | Crowley | 600/440 |
| 5,867,146 A * | 2/1999 | Kim et al. | 345/158 |
| 5,977,958 A * | 11/1999 | Baron et al. | 345/179 |
| 6,004,269 A * | 12/1999 | Crowley et al. | 600/439 |
| 6,118,205 A * | 9/2000 | Wood et al. | 310/316.01 |
| 6,745,632 B1 * | 6/2004 | Dryer et al. | 73/597 |
| 6,771,006 B2 * | 8/2004 | Zioter et al. | 310/334 |
| 6,798,403 B2 * | 9/2004 | Kitada et al. | 345/173 |
| 6,842,716 B1 * | 1/2005 | Leleu | 702/178 |
| 7,336,262 B2 * | 2/2008 | Tsuji | 345/173 |
| 8,280,692 B2 * | 10/2012 | Kajitani et al. | 702/189 |
| 2003/0052795 A1 * | 3/2003 | Schlick et al. | 340/903 |
| 2003/0144814 A1 * | 7/2003 | Hama et al. | 702/159 |
| 2004/0032399 A1 * | 2/2004 | Sekiguchi et al. | 345/173 |
| 2005/0150697 A1 * | 7/2005 | Altman et al. | 178/19.02 |
| 2008/0084789 A1 * | 4/2008 | Altman | 367/127 |
| 2008/0166048 A1 * | 7/2008 | Raif et al. | 382/187 |
| 2010/0005890 A1 * | 1/2010 | Miyamoto | 73/597 |
| 2010/0228523 A1 * | 9/2010 | Kajitani et al. | 702/176 |
| 2011/0261654 A1 * | 10/2011 | Miyamoto et al. | 367/125 |

FOREIGN PATENT DOCUMENTS

| | | |
|---|---|---|
| JP | 2001119786 A | 4/2001 |
| JP | 2004108826 A | 4/2004 |
| JP | 2005249770 A | 9/2005 |
| JP | 2007139638 A | 6/2007 |
| JP | 2009115735 A | 5/2009 |
| WO | 2008091012 A | 7/2008 |
| WO | 2009028591 A | 3/2009 |

OTHER PUBLICATIONS

Kashiwagi, "M-sequence and its applications", Shokodo Co. Ltd., Mar. 25, 1996, ISBN4-7856-2128-1.

* cited by examiner (a) M-SEQUENCE PHASE-MODULATED SIGNAL (0/1 BIT CORRESPONDS TO 1-/1)

(b) FREQUENCY CHARACTERISTICS OF M-SEQUENCE PHASE-MODULATED WAVE (a) USING REFERENCE WAVEFORM WITHOUT FILTRATION
(DIFFERENCE BETWEEN FIRST AND SECOND PEAKS OF CORRELATION
VALUE IN LOWER GRAPH IS SMALL AS ABOUT 0.1)

(b) USING REFERENCE WAVEFORM AFTER FILTRATION
(DIFFERENCE BETWEEN FIRST AND SECOND PEAKS OF
CORRELATION VALUE IN LOWER GRAPH IS LARGE AS ABOUT 0.4)

(a)

(b)

ULTRASONIC WAVE PROPAGATION TIME MEASUREMENT SYSTEM

TECHNICAL FIELD

Related Application

This application claims the benefit of Japanese Patent Application No. 2009-042127, filed Feb. 25, 2009, which is hereby incorporated by reference herein in its entirety.

This invention relates to a method for measuring an ultrasonic wave propagation time between an ultrasonic wave source and a specified position and an ultrasonic wave propagation time measurement system. More particularly, the invention relates to a method and a system for measuring an ultrasonic wave propagation time whereby audible noise produced at the time of transmission of the ultrasonic wave is reduced.

BACKGROUND

Patent Document 1 is an example that discloses a method to determine a distance using a reception time lag between an infrared ray signal and an ultrasonic wave signal. Patent Document 2 discloses an electronic pen system as an example of a conventional position detection method using an ultrasonic wave. The position detection system includes an electronic pen having a function to transmit an ultrasonic wave signal having a specified waveform in a constant period and an infrared ray trigger signal in a fixed period and a reception portion to receive transmitted two signals, and the reception portion determines the position of the electronic pen by the arrival time of the trigger signal and the arrival time of the ultrasonic wave.

Patent Document 3 discloses a method to eliminate reverberation for an ultrasonic wave transmission/reception system by assigning a band width of impedance of an ultrasonic sensor, transmission band width of a transmission means, reception band width of a reception means and pass-band width of a transmission/reception switching circuit in a predetermined relation.

PRIOR ART DOCUMENT

Patent Document

[Patent Document 1]
Japanese Patent Kokai Publication No. JP2007-139638A
[Patent Document 2]
U.S. Pat. No. 6,118,205
[Patent Document 3]
Japanese Patent Kokai Publication No. JP200'-119786A

SUMMARY

It should be noted that the contents disclosed in Patent Documents 1 to 3 are hereby incorporated by reference herein in their entirety. The following analyses are given by the present invention.

Because a frequency beyond an audible band range should be used for an ultrasonic wave signal that is transmitted from an ultrasonic wave source, the signal should be 20 kHz or more. A speaker, which can electronically oscillate a small and rigid diaphragm, is known as a means for producing such a signal having the frequency band range with sufficient sound pressure. However, it is difficult to mount such a speaker on a small movable object such as an electronic pen because it's difficult to make such a speaker small and it is current-driven and consumes a large amount of electricity. Thus, a piezoelectric element of a voltage-driven type is widely used as an ultrasonic wave transmission source.

A piezoelectric element generally consumes a small amount of electricity because it is a voltage-driven type, and is usually combined with a resonance body having a low sound impedance for realizing sufficient sound pressure. When using a resonance phenomenon, however, although it is possible to transmit ultrasonic wave by a specified phase, frequency and gain, a transmission gain in other frequency range is rather low and thus it is difficult to use various kinds of modulation methods. It is also difficult to transmit ultrasonic wave that can follow up modulation wave by any modulation method because a piezoelectric element itself has a large mechanical Q value and it causes long residual vibration. In addition, because it uses resonance characteristics, the resonance frequency or peak gain may vary widely by a small offset of the material characteristics and its shape of the piezoelectric element.

On the other hand, for continuous measurement of propagation time, an ultrasonic wave has to be transmitted synchronously based on a trigger signal having a constant period. The constant period differs depending on a required accuracy and/or a relative displacement speed between an ultrasonic wave source and a receiver. When applying to an electronic pen or the like, at least 20 ms or less is required for writing without stress by human. When an ultrasonic wave signal having a frequency of 20 kHz or more is transmitted into space by the constant period of 20 ms, although the ultrasonic wave signal itself is not audible to the human, the single or burst signal having the constant period of 20 ms becomes audible as a sound of 50 Hz.

Because the sound pressure is proportional to the signal strength and the number of a succession of the bursts of the single or burst signal, the ultrasonic wave signal used for an electronic pen or the like is generally composed of one to three waves. A signal having such a number of the waves is almost inaudible when being about 30 to 50 cm apart from the source of the ultrasonic wave signal and one can write without stress.

Because a range of audible sound that makes human unpleasant differs relatively greatly between individuals, filtering for suppressing the sound pressure that is effective for only specified frequency ranges may cause an adverse effect when applied for unspecified users.

It is an object of the present invention to provide a method and a system by which a propagation time of an ultrasonic wave signal transmitted from a movable object can be measured accurately while audible noise produced at the time of transmission of the ultrasonic wave signal is reduced.

In a first aspect of the present invention, there is provided an ultrasonic wave propagation time measurement system that comprises: a transmitting section that transmits an electromagnetic wave signal indicating transmission timing and an ultrasonic wave signal, and a receiving section that detects the transmitted electromagnetic wave signal and the ultrasonic wave signal and calculates an ultrasonic wave propagation time based on reception times of the electromagnetic wave signal and the ultrasonic wave signal. An initial mode setting mechanism that constitutes an optimum ultrasonic wave transmission/reception system by selecting one or more set values of setting parameters is provided in a controlling unit that controls transmission of the signals in the transmitting section and in a data processing unit that controls detection and calculation in the receiving section. In the present invention, the "mechanism" (function unit) includes an electronic structure as well as a mechanical structure.

According to an ultrasonic wave propagation time measurement system of the present invention, the transmitting unit comprises an electromagnetic wave transmitting section that is driven by an electromagnetic wave driving unit and transmits the electromagnetic wave signal indicating transmission timing, an ultrasonic wave driving signal generating unit that generates an ultrasonic wave driving signal by modulating an ultrasonic wave at the same time of the transmission of the electromagnetic wave signal based on a pseudo random signal of high self-correlativity, and an ultrasonic wave transmitting unit that is driven by the ultrasonic wave driving signal and transmits an ultrasonic wave signal having a higher frequency than a basic frequency of the ultrasonic wave driving signal, and is made of a piezoelectric element or a magnetostriction element; and the receiving section comprises an electromagnetic wave receiving unit that detects the transmitted electromagnetic wave signal, an ultrasonic wave receiving unit that detects the transmitted ultrasonic wave signal, a data processing unit that calculates a correlation value between the detected ultrasonic wave signal and a model waveform that has the same waveform as the ultrasonic wave driving signal, detects a main peak value of the calculated correlation value, and calculates ultrasonic wave propagation time based on a detected time of the electromagnetic wave signal and a detected time of the main peak value, an ultrasonic wave filtration unit that relates to the ultrasonic wave driving signal generating unit and filtrates the ultrasonic wave for transmission, and a measurement unit that relates to the data processing unit and determines sound pressure and frequency of the received ultrasonic wave. The system also comprises an initial mode setting mechanism that constitutes an optimum ultrasonic wave transmission/reception system by selecting one or more set values of setting parameters in a controlling unit that controls the transmission of the signals in the transmitting section and in a data processing unit that controls the detection and the calculation in the receiving section.

In a second aspect of the present invention, there is provided a method for measuring an ultrasonic wave propagation time in which an electromagnetic wave signal indicating transmission timing and an ultrasonic wave signal are transmitted and the propagation time is determined based on reception times of the electromagnetic wave signal and the ultrasonic wave signal. The method comprises a step of setting an initial mode by selecting a setting value from a plurality of alternatives for at least one parameter selected from the group consisting of an ultrasonic wave driving signal pattern, ultrasonic wave driving frequency, ultrasonic wave filtration characteristics and transmission timings of the electromagnetic wave signal and the ultrasonic wave signal.

In accordance with an ultrasonic wave propagation time measurement system of the present invention, a propagation time of an ultrasonic wave signal can be measured accurately while sound in the audible range (i.e., audible noise) produced at the time of transmission of the ultrasonic wave signal is effectively reduced.

PREFERRED MODES

Figure 1:
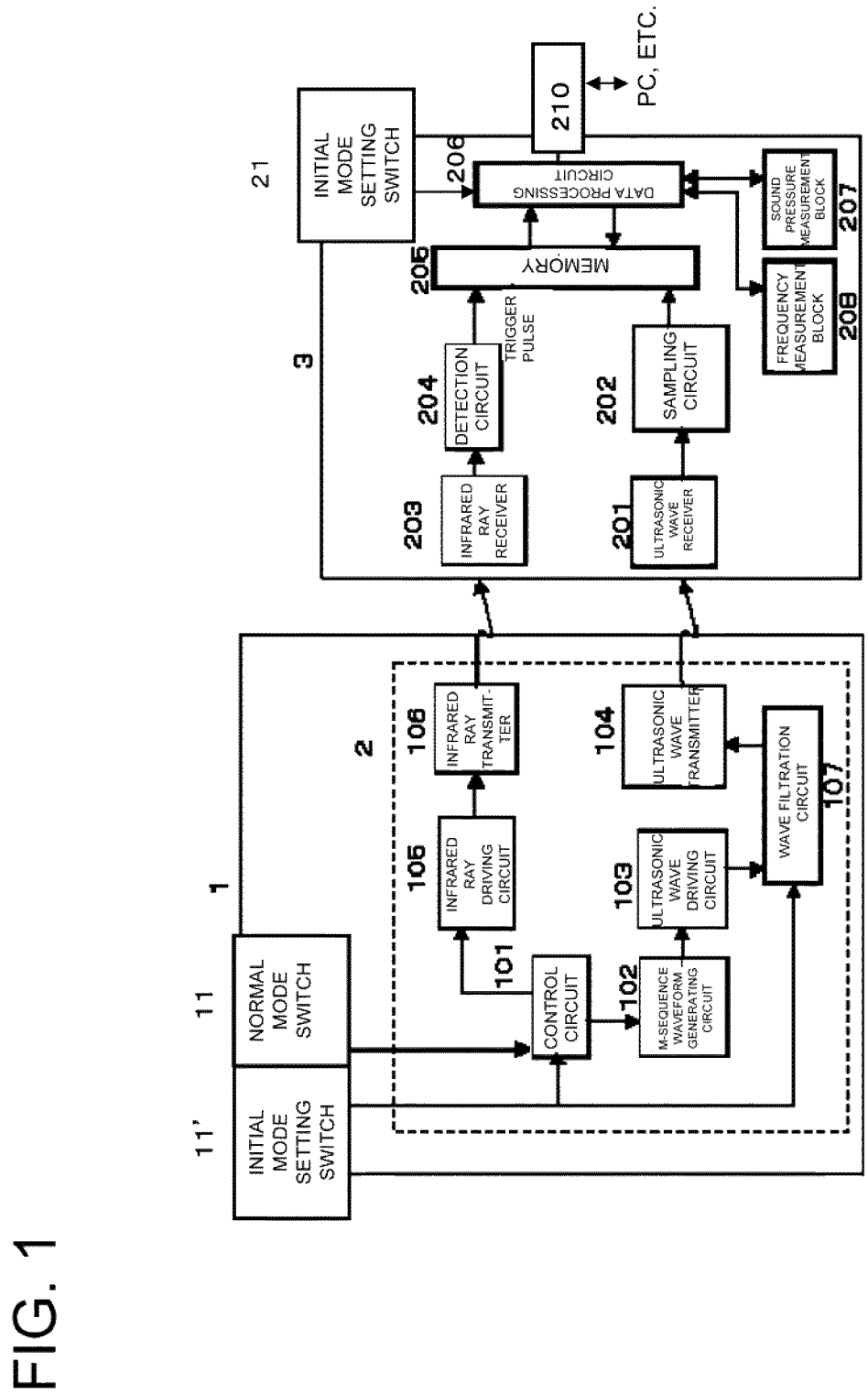
FIG. 1 is a block diagram illustrating a first exemplary embodiment of an ultrasonic wave propagation time measurement system of the present invention (an electronic pen system)

Preferably, the ultrasonic wave propagation time measurement system of the present invention includes an input/output unit that allows data input/output between the data processing unit and outside.

Preferably, the system includes a communication portion that allows communication between the controlling unit and the data processing unit.

Preferably, the controlling unit includes a mechanism (function unit) that changes an ultrasonic wave driving signal pattern modulated by the pseudo random signal of high self-correlativity by selecting one of parameter set values stored in the controlling unit or inputted from outside.

Preferably, the controlling unit includes a mechanism that changes an ultrasonic wave driving frequency by selecting one of parameter set values stored in the controlling unit or inputted from outside.

Preferably, the controlling unit includes a mechanism that changes transmission timings of the electromagnetic wave signal and the ultrasonic wave signal by selecting one of parameter set values stored in the controlling unit or inputted from outside.

Preferably, the controlling unit includes a mechanism that changes a wave filtration frequency by selecting one of parameter set values stored in the controlling unit or inputted from outside.

Preferably, the controlling unit includes a mechanism that changes a wave filtration gain by selecting one of parameter set values stored in the controlling unit or inputted from outside.

Preferably, the ultrasonic wave receiving unit is constituted of one selected from the group consisting of a piezoelectric element, a magnetostriction element and a microphone.

Preferably, the ultrasonic wave driving signal is modulated by applying ultrasonic wave M period, where M is an integer of 1 or more, per one bit of the pseudo random signal.

Preferably, the ultrasonic wave driving signal generating unit phase-modulates the ultrasonic wave.

Preferably, the pseudo random signal is an M-sequence data. Because the frequency of the transmitted ultrasonic wave is larger than the driving frequency as to a frequency of a model wave modulated by the M-sequence, reproducibility of the modulated wave can be improved and thus it becomes possible to increase correlativity between a reception wave and the model wave. The noise of the whole system can be reduced by selecting bit series of an M-sequence data.

Preferably, a wave filtration unit for removing driving signal of audible range is provided in an ultrasonic wave generating circuit that constitutes the ultrasonic wave transmitting unit. According to this structure, intensity of the sound (acoustic) wave of audible range can be more reduced and stress against human is expected to be reduced.

Preferably, a wave filtration unit is provided, in an ultrasonic wave generating circuit that constitutes the ultrasonic wave transmitting unit, for removing sound wave of frequency range corresponding to at least a transmission period of the ultrasonic wave.

Preferably, a wave filtration unit is provided, in an ultrasonic wave generating circuit constituting the ultrasonic wave transmitting unit, for removing sound wave of a frequency range corresponding to at least a modulation period of the M-sequence code.

Preferably, a sound wave just after transmitted into space from the ultrasonic wave transmitting unit having the filtration unit in the ultrasonic wave generating circuit is used as a model waveform for the correlation calculation.

Preferably, the M-sequence data is a code of 15 bits generated by a fourth degree characteristic polynomial and a last part of the bit series is a row (sequence) of 1111 or 000.

Preferably, the M-sequence data is a code of 15 bits generated by a fourth degree characteristic polynomial and a last part of the bit series is a row (sequence) of 1111000.

EXEMPLARY EMBODIMENTS

Exemplary Embodiment 1

Next, exemplary embodiments of the present invention will be explained in detail taking an electronic pen system as an example with reference to FIGS. 1 to 10. However, the present invention can also be applied to a robot system in which an ultrasonic wave transmitting unit is provided on an obstacle and a receiving section is provided on a robot, and the robot is controlled to avoid the obstacle by calculating a distance from the obstacle or to a medical nursing system in which an ultrasonic wave transmitting unit is attached on a patient and the position of the patient is determined.

A phase modulation using an M-sequence signal that is a pseudo random signal and has high self-correlativity is adopted as a modulating method of the ultrasonic wave; however, other modulating methods are also expected to obtain the same effect. In addition, a pseudo random signal having high self-correlativity is sufficient for a signal sequence as a basis of the modulation and thus a so-called gold sequence signal may be used to obtain the same effect.

When using an ultrasonic wave signal modulated by the pseudo random signal having high self-correlativity according to the present invention, a number of waves of the ultrasonic wave signal is larger than that of a burst signal that is used in the conventional art. For example, when modulating an ultrasonic wave signal by using an M-sequence signal, at least fifteen (15) waves are necessary and it causes generation of sound (noise) having five times or more energy level than that generated from a conventional electronic pen and the like, and the noise may sometimes exceed a level that one can write without stress by the noise.

As a feature of the M-sequence code, a period of reversal of the codes may range from 1 code to 4 codes and thus there is a strong possibility that a sound peak exists at a frequency of a half, a third and a fourth of a frequency of the ultrasonic wave transmitting signal. If the frequency reaches the audible range, intensity of the noise upon transmission of the ultrasonic wave is increased and it causes stress to human when writing. These problems inevitably occur when an ultrasonic wave signal is modulated by a specific method and a number of waves is increased.

FIG. 1 is an exemplary embodiment of an ultrasonic wave propagation time measurement system according to the present invention and shows a block diagram of an electronic pen system using an ultrasonic position determination system according to the present invention. The system is composed of an electronic pen 1 comprising switches 11 and 11' and a transmitting section 2 and a receiving section 3 located at a predetermined position apart from the transmitting section. The transmitting section 2 is composed of a control circuit 101, M-sequence (waveform) generating circuit (or M-sequence bit series storing memory) 102, ultrasonic wave driving circuit 103, ultrasonic wave transmitter (piezoelectric element or magnetostriction element) 104, infrared ray driving circuit 105, infrared ray transmitter 106, and wave filter (wave filtration circuit) 107.

Figure 3:
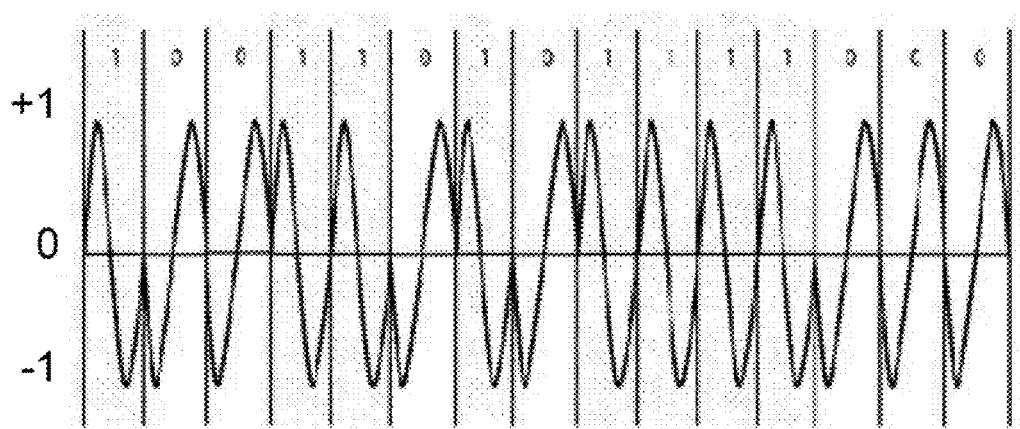
FIG. 3 is an example of a waveform diagram of an ultrasonic wave driving signal that is phase modulated by an M-sequence data.

The M-sequence generating circuit 102 generates an M-sequence determined by a characteristic polynomial based on an M-sequence initial condition provided by the control circuit 101. For example, the M-sequence generating circuit 102 has a 4-bits shift register having a quality of a fourth degree characteristic polynomial of $f(x)=x^4+x+1$ or $f(x)=x^4+x^3+1$ and generates a bit-series having a sequence length of 15 bits. By changing the initial condition, fifteen different data that an arrangement of data is shifted rotationally are obtained. FIG. 3 shows an example of an ultrasonic wave driving signal waveform that is phase-modulated by an M-sequence. Each bit of the fifteen bits M-sequence data of. "000100110101111" corresponds to one period of a basic wave. When the bit is zero, the phase is inversed and when the bit is 1, the phase is not inversed. The modulated wave has a length of fifteen periods of the basic wave. Details of M-sequence is described in "M-sequence and its application" by Jun Kashiwagi, 25 Mar. 1996, Syokodo, and the like.

When the normal mode switch 11 provided in the electronic pen 1 is pressed, the control circuit 101 provides a trigger signal as a criterion (reference) of time measurement and 4-bits initial condition data for M-sequence to the infrared ray driving circuit 105 and the M-sequence generating circuit 102. The infrared ray transmitter 106 is activated by an output of the infrared ray driving circuit 105 and transmits infrared ray into space from the electronic pen.

On the other hand, the M-sequence generating circuit 102 generates an M-sequence bit-series based on the initial condition supplied by the control circuit 101 and supplies the bit-series to the ultrasonic wave driving circuit 103. The ultrasonic wave driving circuit 103 phase-modulates an ultrasonic wave signal using the M-sequence and supplies it as an ultrasonic wave driving signal to the ultrasonic wave transmitter 104 via the wave filter 107. The ultrasonic wave transmitter 104 is driven (activated) by the driving signal and transmits an ultrasonic wave signal phase-modulated by the M-sequence into space in synchronism with transmission timing of the infrared ray transmitter 106. Therefore, the infrared signal and the ultrasonic wave signal are transmitted from the electronic pen at the same time toward the receiving section. The above steps are repeated at a certain fixed period during the switch is pressed so as to make an electronic pen function.

Because the control circuit 101 is composed of CPU and the like, a rectangular wave is generally used for each signal waveform. As to the infrared trigger signal as a reference signal for time measurement, it is desirable to be a rectangular wave as much as possible to make time difference against the sampling time on the receiver side small and make determination error as minimum as possible. As to the ultrasonic wave signal, even when the driving waveform is rectangular, the ultrasonic wave transmitted into space becomes a pseudo sine wave because the ultrasonic wave transmitter 104 is mainly composed of a piezoelectric element (or magnetostriction element) and the piezoelectric element itself contains L- and C-components. As to the waveform of transmitter side, a sine wave, rectangular wave, triangle wave or trapezoid wave does not cause any problem with consideration of characteristics of the transmitter.

The receiving section 3 is composed of an ultrasonic wave receiver (piezoelectric element, magnetostriction element or microphone) 201, sampling circuit 202, infrared ray receiver 203, detection circuit 204, memory 205 and data processing circuit 206. The data processing circuit 206 comprises a sound pressure measurement block 207 and a frequency measurement block 208 for the ultrasonic wave.

The ultrasonic wave receiver (piezoelectric element, magnetostriction element or microphone) 201 receives the ultrasonic wave signal transmitted from the electronic pen 1 and converts it into an electric signal. The sampling circuit 202 samples the ultrasonic wave signal at constant intervals and stores them in the memory 205 as phase-modulated M-sequence ultrasonic wave data.

The infrared ray receiver 203 receives the infrared ray signal from the electronic pen 1 and converts it into an electric signal. The detection circuit 204 stores a reception time of a trigger pulse into the memory 205 upon detection of the trigger pulse from the output of the infrared ray receiver 203. The detection circuit 204 stores an M-sequence initial condition data into the memory 205 upon detection of it.

As a substitute for the M-sequence initial condition being included in the infrared ray signal, it is possible to store a phase-modulated M-sequence ultrasonic wave model waveform previously generated by a determined M-sequence initial condition in the memory 205 and make the data processing circuit 206 read the M-sequence model waveform upon receiving the infrared trigger signal.

The data processing circuit 206 generates the M-sequence model waveform from the stored M-sequence initial data upon reading a data from the memory 205 indicating an arrival of the trigger pulse, phase-modulates the model waveform by the ultrasonic wave likewise in the case of the transmitting section 2 and generates a phase-modulated ultrasonic wave M-sequence model waveform that has the same waveform as the ultrasonic wave driving signal of the transmitter side. The data processing circuit 206 performs a correlation processing between the phase-modulated ultrasonic wave model waveform and the phase-modulated ultrasonic wave reception waveform stored in the memory 205. The data processing circuit 206 calculates, upon detecting the first peak (main peak) of a correlation value, a time elapsed from an arrival time of the trigger pulse to a detection time of the correlation peak, which is to say a propagation time of the ultrasonic wave signal from the electronic pen 1 to the receiving section 3.

In specific terms, the data processing circuit sets the trigger detection time stored in the memory 205 as a sampling starting time (t), reads the phase-modulated M-sequence ultrasonic wave data from the memory 205 and calculates the correlation value C(t) at the sampling starting time (t) between the read data and the generated phase-modulated M-sequence ultrasonic wave model waveform based on a numerical formula (1).

(Numerical formula 1)

$$C(t) = \frac{1}{N}\sum_{i=0}^{N-1} r(i)f(i+t) \quad (1)$$

In the formula (1), i is an integer and a variable of the sampling time, N is a number of samplings of the model waveform, r(i) is a value of the model waveform at a sampling time of i, and f(i+t) is a value of the received waveform at a sampling time of (i+t).

Next, a peak value is searched based on the obtained correlation value. When no peak value is detected, the sampling starting time (t) is incremented by 1 unit and a peak value is searched repeatedly in the same way. When a correlation peak value is detected, the data processing circuit reads a sampling time corresponding to the variable t at the detection time of the correlation peak value from the memory 205. Finally, the data processing circuit 206 calculates the propagation time from the electronic pen 1 to the receiving section 3 based on the detection time of the trigger and the detection time of the peak value. Suppose that the sampling time of the reception of the infrared ray trigger pulse is zero and a sampling period is DT, the ultrasonic wave propagation time can be calculated by t×(multiplies) DT.

Figure 5:
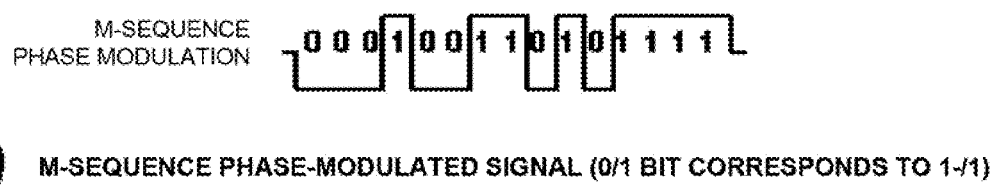
FIG. 5 is an example of ultrasonic wave frequency characteristics modulated by a bit series of M-sequence.
Figure 5:
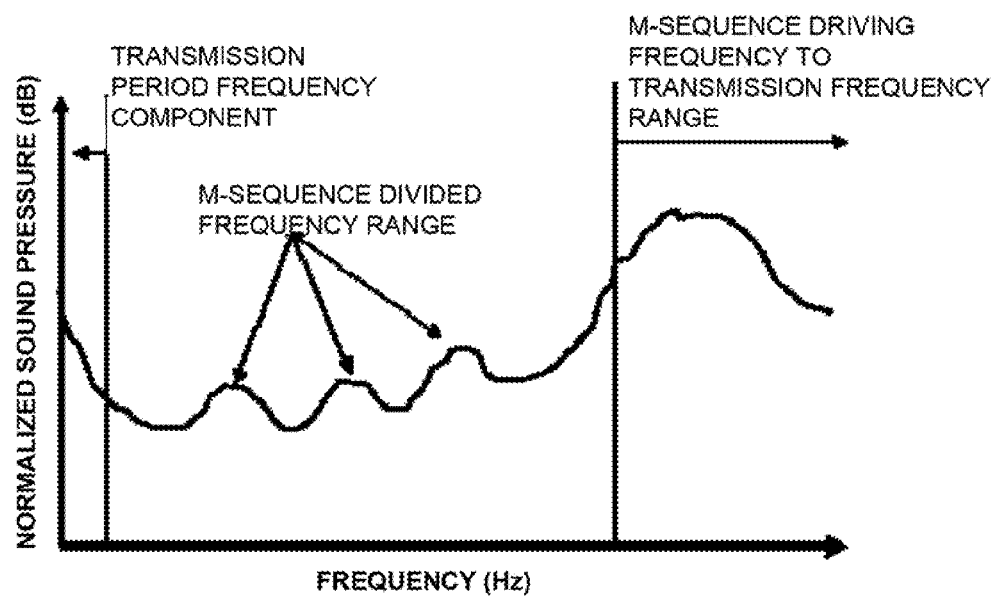

It becomes possible to realize writing/drawing by an electronic pen based on the basic measurement of the ultrasonic wave propagation time by the method above explained. FIG. 5 shows frequency characteristics of an ultrasonic wave transmitted from an electronic pen having no wave filter (wave filtration circuit) in the transmitting section 2 in the electronic pen. The ultrasonic wave driving signal modulated by the M-sequence bit series has characteristics substantially close to a rectangular wave shown in (a) of FIG. 5. Therefore, a portion (segment) having a bit pattern of "10" or "01" has a frequency equal to the driving signal frequency; however, a portion having a bit pattern of "1100" or "0011" is equal to be driven by a half (½) frequency. Similarly, a third (⅓) and a fourth (¼) frequency components are contained in the driving frequency. Therefore, the ultrasonic wave signal transmitted into space has a half, a third and a fourth frequency components of the driving frequency with high sound pressure, and thus, when such frequencies are in an audible range, they become audible to human.

There may be a case in applications to an electronic pen and the like where it causes stress to human because the ultrasonic wave modulated by M-sequence has at least 15 waves and the number of waves is larger than a conventional frequently-used burst wave having 1 to 3 waves, and thus sound wave energy is also increased. In addition, a transmission period of the ultrasonic wave is generally 10 to 20 ms and the ultrasonic wave generated by this period becomes a noise of 50 to 100 Hz as viewed in a macroscopic level. The noise of this frequency range becomes audible like humming "JIRI JIRI" and it may cause a stress factor. To avoid this, a wave filter may be provided in the transmitting section 2 in an electronic pen so as to suppress audible noise and use it as a means to make a comfortable electronic pen system.

In addition, by providing a means capable of measurement of frequency and sound pressure of an ultrasonic wave in the receiving section 3, it becomes possible to set optimum ultrasonic wave driving conditions according to the change of the ultrasonic wave driving frequency and its sound pressure and to absorb variation (fluctuation) of performance (the variation is rather wide because it uses resonance phenomenon) in fabrication of a piezoelectric element, etc. resulting in a high speed and high precision measurement for a propagation time of an ultrasonic wave.

It also becomes possible to realize noise reduction by selecting specified M-sequence bit series pattern because it becomes possible to measure sound pressure change of received ultrasonic wave caused by the change of M-sequence bit series pattern of the ultrasonic wave transmitter side.

The noise-reduced, high speed and high precision ultrasonic wave propagation time measurement system above explained can be achieved by the following steps. At first, the ultrasonic wave sound pressure measurement block 207 and frequency measurement setting block 208 in the receiving section 3 and the control circuit 101 in the transmitting section 2 of the electronic pen 1, as shown in FIG. 1, are activated by the initial mode setting switch 21 of the receiving section 3 and the initial mode setting switch 11' of the electronic pen 1, respectively. The setting of the initial mode can be carried out by mechanical switches, etc. and it is also possible to set the initial mode of the receiving section 3 side from outside via an input/output unit 210 that is configured so as to be connected to PC (personal computer), for example.

Then different patterns of M-sequence bit series are transmitted one after another from the transmitting section 2 of the electronic pen 1 and the receiving section 3 determines the M-sequence bit series pattern that makes the sound pressure of the received ultrasonic wave smallest by measuring and comparing peak values or mean sound pressures of the sound pressures of the received ultrasonic waves.

Next, signals, each having an altered (modulated) driving frequency, are transmitted from the transmitting section 2 of the electronic pen 1 in a predetermined pattern and then the receiving section 3 calculates correlation values between the received waveforms and the model waveform and determines the driving frequency that has the highest correlation value. In this case, the model waveform has to be changed at the receiving section 3 side, and the changing can be performed easily by transmitting an infrared ray signal trigger pattern corresponding to each driving frequency. Even when such infrared ray signals are not used, it can be also performed by continuous alteration (modulation) of the model waveform in a predetermined range and steps.

Next, ultrasonic waves having specified patterns generated by the wave filter (wave filtration circuit) 107 whose attenuation rate and pole frequency are changed in turn are repeatedly transmitted in turn, and then an operator inputs the pattern that generates smallest writing noise by selecting and inputting the pattern via the input/output unit 210 or selecting/determining the pattern using the initial mode setting switches 11' and 21. Finally, by changing generation intervals of the infrared ray signal and the ultrasonic wave signal, the operator determines a configuration of the electronic pen 1 and the receiving section 3 by selecting the periods that the operator feels the noise smallest using the initial mode setting switch 11' and 21 and/or by inputting from outside.

The initial mode setting switch can be realized using a DIP switch and the like connected to the control circuit 101 of the transmitting section 2 of the electronic pen 1 and to the data processing circuit 206 of the receiving section 3, as well as other conventional switches. The receiving section 3 can be set via the input/output unit 210, as well. The precision of the propagation time measurement of an ultrasonic wave can be improved and high speed, low noise and comfortable writing/drawing can be realized by applying the structure above explained.

Exemplary Embodiment 2

Figure 2:
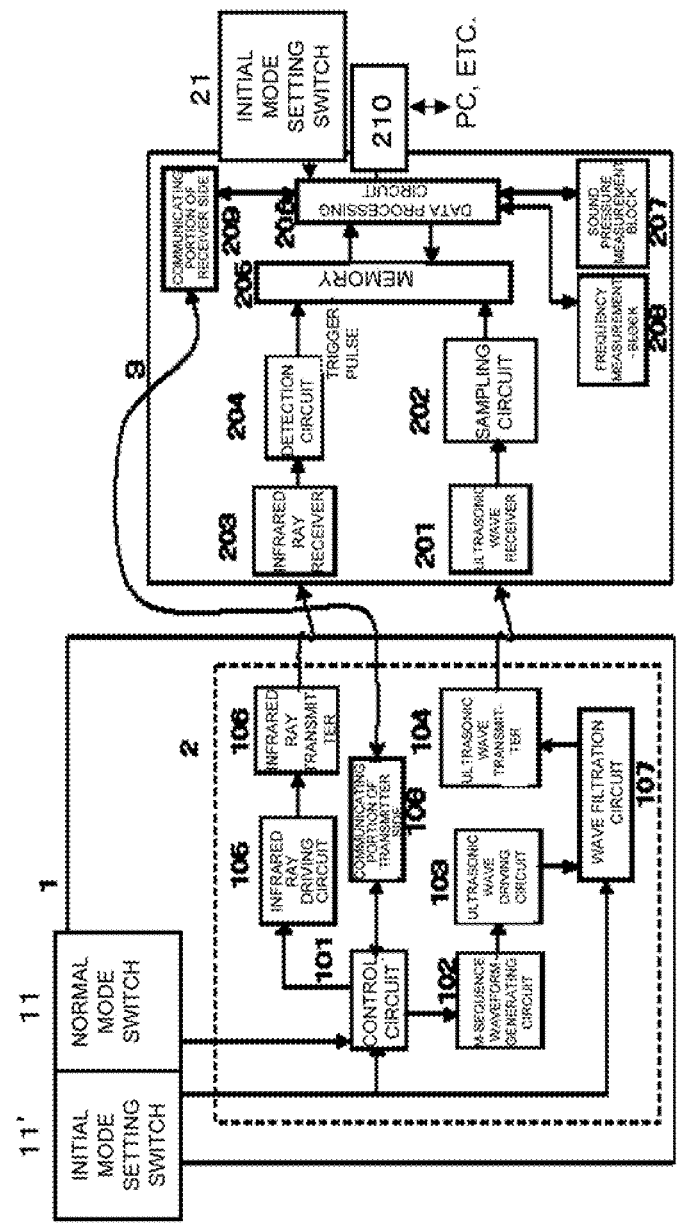
FIG. 2 is a block diagram illustrating a second exemplary embodiment of an ultrasonic wave propagation time measurement system of the present invention (an electronic pen system)

FIG. 2 shows a second exemplary embodiment, in which a communicating unit is provided in each of the transmitting section 2 of the electronic pen 1 and the receiving section 3. A communicating unit 108 of transmitter side in the electronic pen 1 is connected to the control circuit 101 and a communicating unit 209 of receiver side in the receiving section 3 is connected to the data processing circuit 206. Once the characteristics of the M-sequence pattern, driving frequency and wave filter (wave filtration circuit) are determined by the same procedure as an exemplary embodiment 1 via the input/output unit 210 connected to the receiving section 3, the characteristics of the electronic pen 1 can be set automatically based on the data through communication between the electronic pen 1 and the receiving section 3. It is also possible to store the setting data for the electronic pen 1 in the receiving section 3 side so that a plurality of electronic pens can be optimized for one receiving section. A method of communication is not limited and may be wire communication or wireless communication, for example.

FIG. 3 is an example of an ultrasonic wave driving signal that is phase-modulated by an M-sequence data. This signal corresponds to a bit series of "100110101111000" and fifteen (15) M-sequences can be generated by circulating the bit series. Practically, reduction of noise of an electronic pen system can be realized by transmitting ultrasonic wave driving signals modulated by the fifteen M-sequence data in turn from the electronic pen using a piezoelectric element, measuring the sound pressure of the ultrasonic wave signals received by the receiving section 3, and selecting the pattern by which smallest peak value or mean sound pressure, etc. is obtained.

Figure 4:
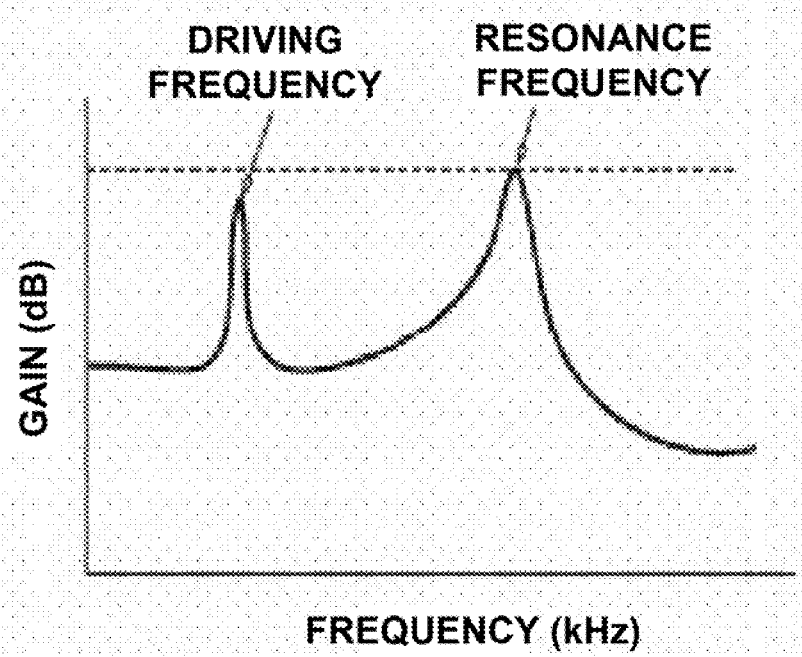
FIG. 4 is an example of an ultrasonic wave reception signal modulated by an M-sequence data in which the same bit continues at the last part.

FIG. 4 is an example of frequency characteristics of an ultrasonic wave signal transmitted into space by applying ultrasonic wave driving signal on a piezoelectric element as an example of an ultrasonic wave transmitter 104 of the transmitting section 2 in the electronic pen 1. Because the phase-modulated ultrasonic wave signal having a wide frequency range should be transmitted using a piezoelectric element of a narrow frequency range, the piezoelectric element is driven by a phase-modulated signal of lower frequency than the resonance frequency of the piezoelectric element for including wide frequency range as much as possible so as to improve correlativity characteristics of the phase-modulated portion and to improve signal identification capability. One of the best conditions is a case where the ultrasonic wave driving frequency is a half (½) of the resonance frequency of the piezoelectric element.

A resonance frequency and a peak gain of a piezoelectric element depend greatly on a shape, material characteristics and fabrication (or assembling) accuracy of the piezoelectric element. Therefore, as far as the driving frequency is variable, the relation between the resonance frequency and the driving frequency can be maintained to be 2:1 and the cause of low yield can be absorbed satisfactorily. Thus a high speed and high precision system can be achieved stably. Besides, a driving signal gain may be also made variable and the correlation characteristics can be further improved by adjusting the gain.

Figure 10:
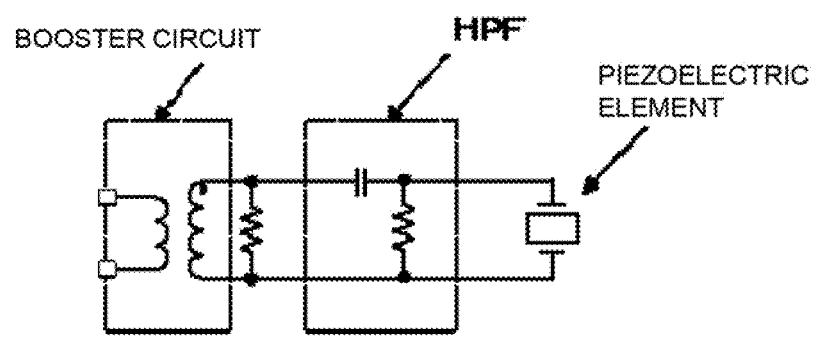
FIG. 10 shows examples of filter circuits provided in a driving circuit (ultrasonic wave generating circuit) of an ultrasonic wave transmitting unit of an electronic pen.
Figure 10:
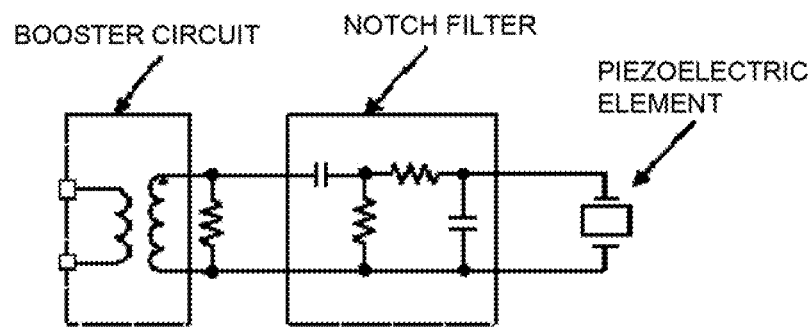

FIG. 10 shows exemplary wave filters to be provided in a driving circuit of a piezoelectric element (ultrasonic wave transmitter) 104 of the transmitting section 2 in the electronic pen 1. A circuit (a) is an example of a wave filtration circuit that cuts low range and a circuit (b) is an example of a wave filtration circuit that cuts only specified frequency range. Such a wave filtration circuit is preferably equipped after a booster circuit because when equipped before a booster circuit for driving a piezoelectric element, characteristics of the booster (generally a coil is used as a transformer) is superposed. Preferably, the circuit is made by a passive component as far as possible because it is equipped in a high voltage portion and is required to be voltage resistant.

Figure 6:
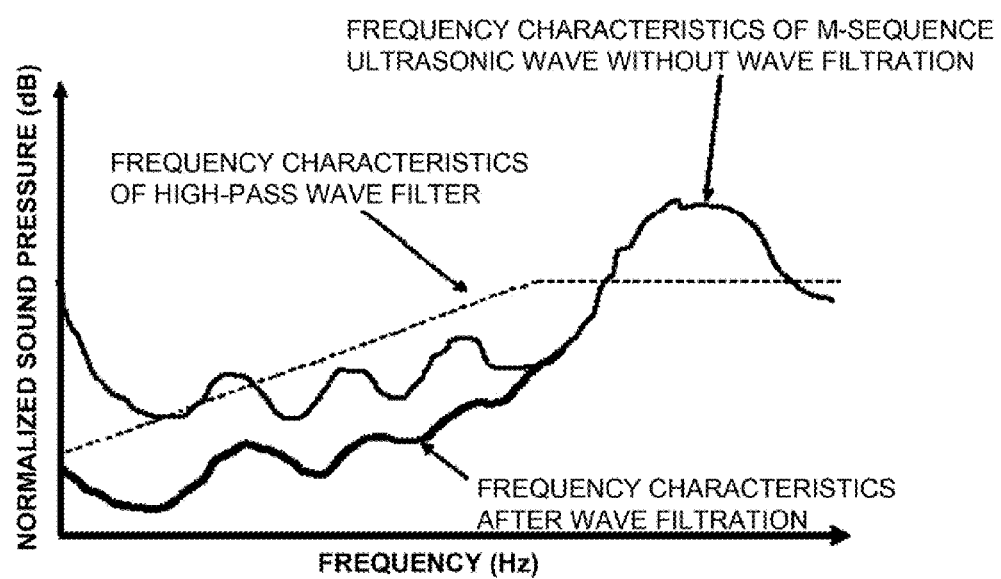
FIG. 6 is a diagram of frequency characteristics of a transmission wave of FIG. 5 after inserting a high-pass filter.

FIG. 6 shows frequency characteristics of a transmission wave after insertion of a high-pass filter. In a case where no wave filter is provided, the frequency characteristics of an ultrasonic wave transmitted from an electronic pen is as indicated in FIG. 5. When a high-pass filter, which passes frequency component that is equal to the driving frequency or more and suppress sound frequency lower than that, is inserted as shown in FIG. 6, the driving period and divided frequencies of the ultrasonic wave driving frequency are damped compared with FIG. 5 and audible sound pressure is greatly suppressed.

Figure 7:
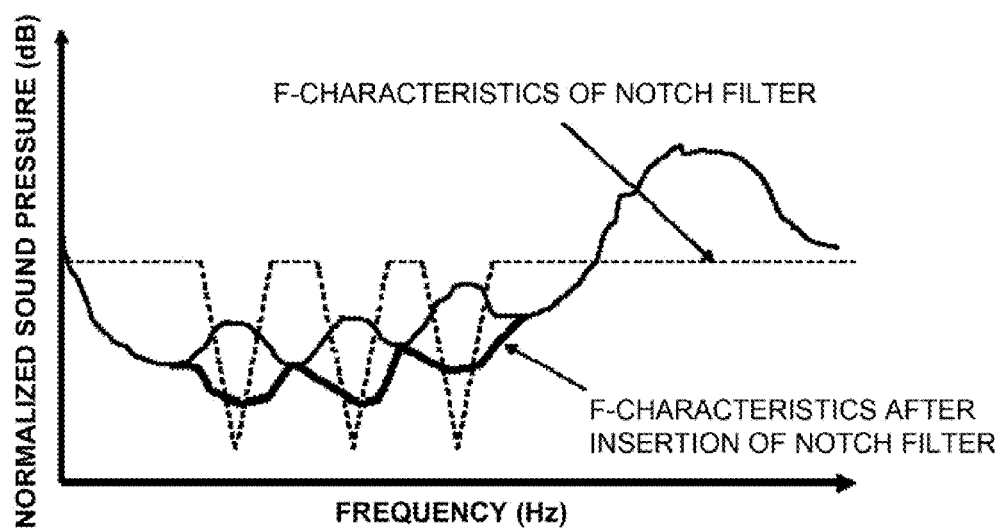
FIG. 7 is a diagram of frequency characteristics of a transmission wave of FIG. 5 after inserting a notch filter in divided frequency regions dependent on the M-sequence.

However, a gain of the phase-modulated portion becomes small and the correlation value tends to decrease because the ultrasonic wave transmission signal has no frequency component of low range. FIG. 7 shows frequency characteristics of the transmission wave after insertion of a notch filter for divided frequency ranges dependent on the M-sequence. As shown in FIG. 7, by applying filtration of frequency ranges concerned only, missing frequency components become small and the decrease of the overall system performance can be minimized and noise reduction can be realized. However, because it causes cost increasing, it is important to select the frequency range of most effective.

Figure 8:
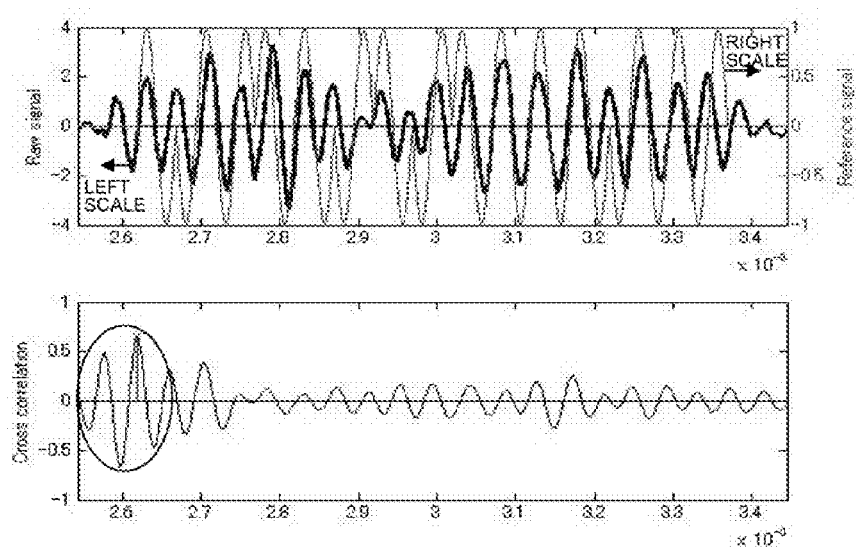
FIG. 8 is a diagram illustrating a change of correlation value when a filtered transmission wave is used as a reference waveform.
Figure 8:
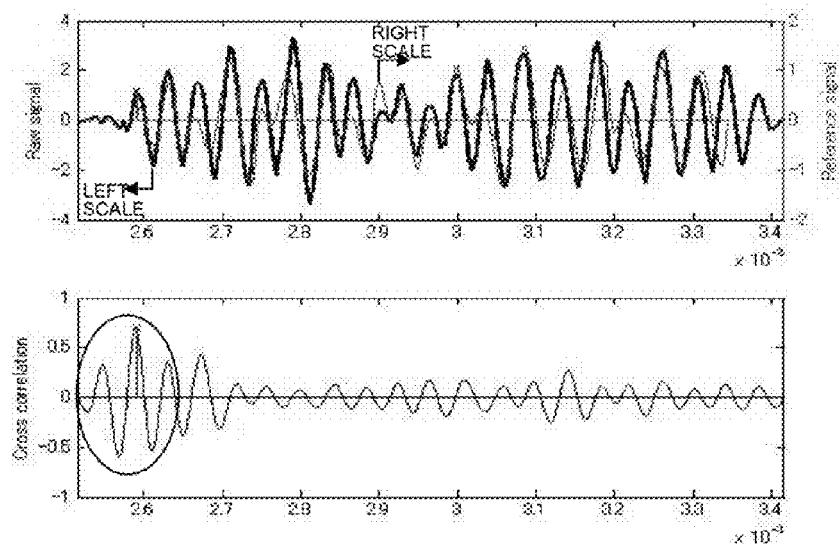

FIG. 8 shows an example of a change of a correlation value of filtered transmission wave used as a reference waveform. The graphs indicate an effect when the ultrasonic wave transmission waveform after filtration is used as a reference waveform for the correlation calculation to complement the missing frequency component. (a) of FIG. 8 is a waveform before filtering and (b) of FIG. 8 is a waveform after filtering. It can be recognized that by using transmission waveform after filtering as a reference waveform, a gain difference between the maximum peak and the previous peak is expanded from 0.1 to 0.4 and it means high possibility of improved precision of peak determination by the correlation calculation.

Figure 9:
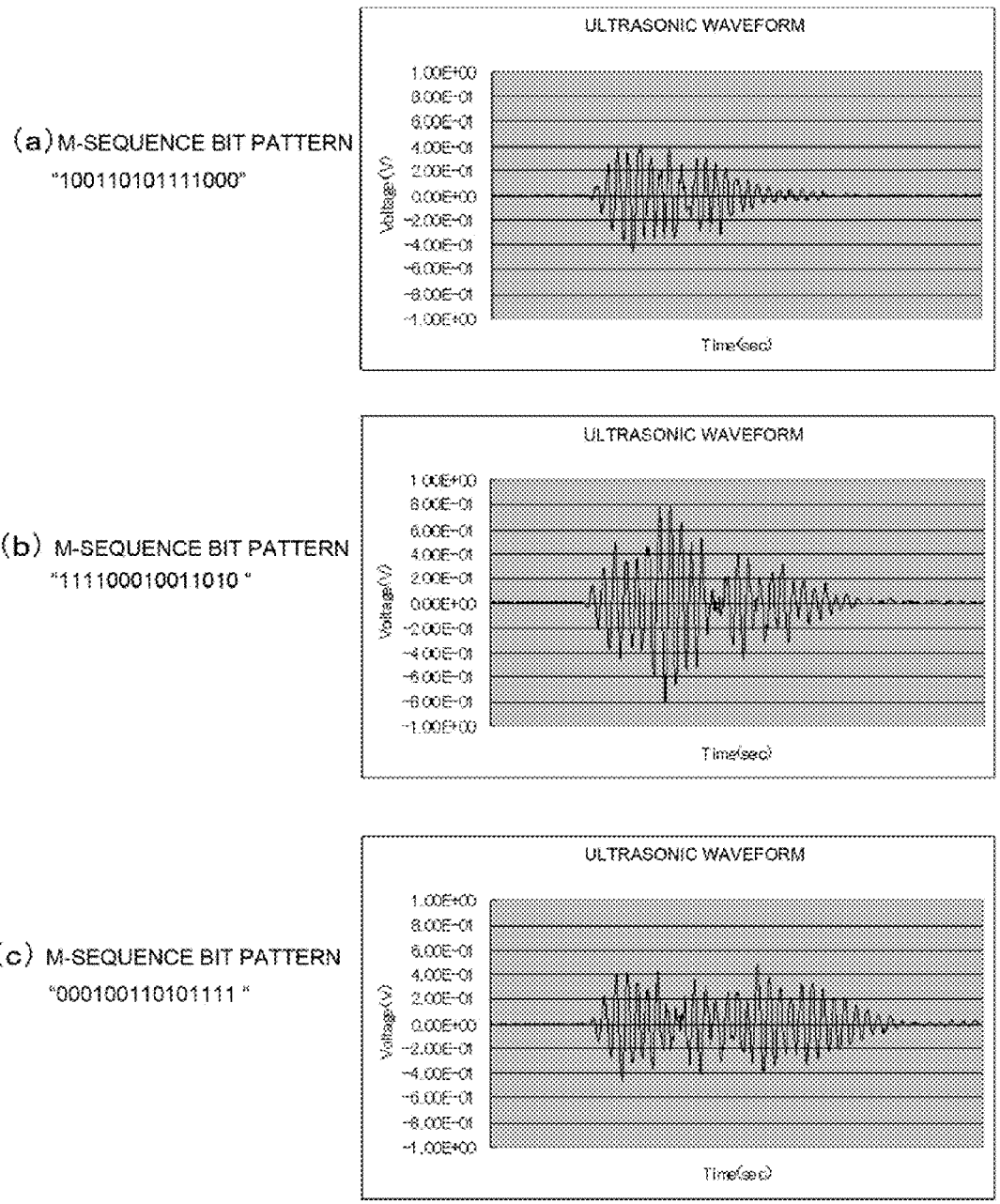
FIG. 9 is a diagram illustrating a change of transmission intensity of ultrasonic waves by selecting a bit series of M-sequence.

(a) to (c) of FIG. 9 are examples in which the sound pressure of ultrasonic wave transmission signal is altered (modulated) by M-sequence bit series. It can be seen that the sound pressure peak becomes smaller as the same bit continues longer at the last part of the M-sequence bit series and that the sound pressure becomes smallest when the last portion of the bit series is "1111000". Noise reduction can be realized by selecting the M-sequence bit series in this way.

As many apparently widely different exemplary embodiments of the present invention can be made without departing from the spirit and scope thereof, it is to be understood that the invention is not limited to the specific exemplary embodiments thereof except as defined in the appended claims.

EXPLANATIONS OF SYMBOLS 1 electronic pen
2 transmitting section
3 receiving section
11 normal mode switch
11' initial mode setting switch
21 initial mode setting switch
101 control circuit
102 M-sequence (waveform) generating circuit
103 ultrasonic wave driving circuit
104 ultrasonic wave transmitter
105' infrared ray driving circuit
106 infrared ray transmitter (electromagnetic wave transmitting unit)
107 wave filter (wave filtration circuit)
108 communicating unit of transmitter side
201 ultrasonic wave receiver (ultrasonic wave receiving unit)
202 sampling circuit
203 infrared ray receiver (electromagnetic wave receiving unit)
204 detection circuit
205 memory
206 data processing circuit
207 sound pressure measurement block
208 frequency measurement block
209 communicating unit of receiver side
210 input/output unit

What is claimed is:

1. An ultrasonic wave propagation time measurement system, comprising:

a transmitting section that transmits an electromagnetic wave signal indicating a transmission timing and an ultrasonic wave signal, and a receiving section that detects the transmitted electromagnetic wave signal and the ultrasonic wave signal and calculates an ultrasonic wave propagation time based on reception times of the electromagnetic wave signal and the ultrasonic wave signal, wherein;

an initial mode setting mechanism that constitutes an optimum ultrasonic wave transmission/reception system by selecting one or more set values of setting parameters is provided in a controlling unit that controls transmission of the signals in the transmitting section and in a data processing unit that controls the detection and the calculation in the receiving section;

and the transmitting section comprises:

an electromagnetic wave transmitting unit that is driven by an electromagnetic wave driving unit and transmits the electromagnetic wave signal indicating transmission timing, an ultrasonic wave driving signal generating unit that generates an ultrasonic wave driving signal by modulating an ultrasonic wave at the same time of the transmission of the electromagnetic wave signal based on a pseudo random signal of high self-correlativity, and an ultrasonic wave transmitting unit that is driven by the ultrasonic wave driving signal and transmits an ultrasonic wave signal having a higher frequency than a basic frequency of the ultrasonic wave driving signal.

2. The ultrasonic wave propagation time measurement system of claim 1, wherein;

the ultrasonic wave transmitting unit is made of a piezoelectric element or a magnetostriction element, and wherein;

the receiving section comprises:

an electromagnetic wave receiving unit that detects the transmitted electromagnetic wave signal, an ultrasonic wave receiving unit that detects the transmitted ultrasonic wave signal, the data processing unit that calculates a correlation value between the detected ultrasonic wave signal and a model waveform that has the same waveform as the ultrasonic wave driving signal, detects a main peak value of the calculated correlation value, and calculates the ultrasonic wave propagation time based on a detected time of the electromagnetic wave signal and a detected time of a main peak value,
an ultrasonic wave filtration unit that relates to the ultrasonic wave driving signal generating unit and filtrates the ultrasonic wave for transmission, and
a measurement unit that relates to the data processing unit and determines sound pressure and frequency of the received ultrasonic wave.

3. The ultrasonic wave propagation time measurement system of claim 2, wherein an input/output unit is provided that allows data input/output between the data processing unit and outside.

4. The ultrasonic wave propagation time measurement system of claim 2, wherein a communicating unit is provided that allows communication between the controlling unit and the data processing unit.

5. The ultrasonic wave propagation time measurement system of claim 2, wherein the controlling unit comprises a mechanism that changes an ultrasonic wave driving signal pattern modulated by the pseudo random signal of high self-correlativity by selecting one of parameter set values stored in the controlling unit or inputted from outside.

6. The ultrasonic wave propagation time measurement system of claim 2, wherein the controlling unit comprises a mechanism that changes an ultrasonic wave driving frequency by selecting one of parameter set values stored in the controlling unit or inputted from outside.

7. The ultrasonic wave propagation time measurement system of claim 2, wherein the controlling unit comprises a mechanism that changes transmission timings of the electromagnetic wave signal and the ultrasonic wave signal by selecting one of parameter set values stored in the controlling unit or inputted from outside.

8. The ultrasonic wave propagation time measurement system of claim 2, wherein the controlling unit comprises a mechanism that changes a wave filtration frequency by selecting one of parameter set values stored in the controlling unit or inputted from outside.

9. The ultrasonic wave propagation time measurement system of claim 2, wherein the controlling unit comprises a mechanism that changes a wave filtration gain by selecting one of parameter set values stored in the controlling unit or inputted from outside.

10. The ultrasonic wave propagation time measurement system of claim 2, wherein the ultrasonic wave receiving unit is constituted of one selected from the group consisting of a piezoelectric element, a magnetostriction element and a microphone.

11. The ultrasonic wave propagation time measurement system of claim 2, wherein the ultrasonic wave driving signal is modulated by applying ultrasonic wave M period, where M is an integer of 1 or more, per one bit of the pseudo random signal.

12. The ultrasonic wave propagation time measurement system of claim 2, wherein the ultrasonic wave driving signal generating unit phase-modulates the ultrasonic wave.

13. The ultrasonic wave propagation time measurement system of claim 2, wherein the pseudo random signal is an M-sequence data; where M is an integer of 1 or more.

14. The ultrasonic wave propagation time measurement system of claim 13, wherein the M-sequence data is a code of 15 bits generated by a fourth degree characteristic polynomial and a last part of the bit series is a row of "1111" or "000".

15. The ultrasonic wave propagation time measurement system of claim 13, wherein the M-sequence data is a code of 15 bits generated by a fourth degree characteristic polynomial and a last part of the bit series is a row of "1111000".

16. The ultrasonic wave propagation time measurement system of claim 2, wherein a wave filtration unit for removing an audible driving signal is provided in an ultrasonic wave generation circuit that constitutes the ultrasonic wave transmitting unit.

17. The ultrasonic wave propagation time measurement system of claim 16, wherein a sound wave just after transmitted into space from the ultrasonic wave transmitting unit having the filtration unit in the ultrasonic wave generation circuit is used as a model waveform for the correlation calculation.

18. The ultrasonic wave propagation time measurement system of claim 2, wherein a wave filtration unit for removing sound wave in a frequency range corresponding to at least a transmission period of the ultrasonic wave is provided in an ultrasonic wave generation circuit that constitutes the ultrasonic wave transmitting unit.

19. The ultrasonic wave propagation time measurement system of claim 2, wherein a wave filtration unit for removing sound wave in a frequency range corresponding to a modulation period of the M-sequence code is provided in an ultrasonic wave generation circuit that constitutes the ultrasonic wave transmitting unit.

20. A method for measuring an ultrasonic wave propagation time wherein an electromagnetic wave signal indicating transmission timing and an ultrasonic wave signal are transmitted and the propagation time is determined based on reception times of the electromagnetic wave signal and the ultrasonic wave signal, comprising:
    setting an initial mode by selecting a setting value from a plurality of alternatives for at least one parameter selected from the group consisting of an ultrasonic wave driving signal pattern, ultrasonic wave driving frequency, ultrasonic wave filtration characteristics and transmission timings of the electromagnetic wave signal and the ultrasonic wave signal;
    wherein the electromagnetic wave signal is transmitted by a process comprising:
    generating an ultrasonic wave driving signal by modulating an ultrasonic wave at the same time of the transmission of the electromagnetic wave signal based on a pseudo random signal of high self-correlativity, and
    transmitting an ultrasonic wave signal having a higher frequency than a basic frequency of the ultrasonic wave driving signal.

* * * * *